United States Patent [19]

Jones et al.

[11] Patent Number: 5,242,625
[45] Date of Patent: Sep. 7, 1993

[54] PREPARATION OF ORGANO-MAGNESIUM HALIDES

[75] Inventors: Raymond V. H. Jones, West Lothian; Robert C. Ewins, Falkirk; Robert M. Mellor, West Lothian, all of Scotland

[73] Assignee: Imperial Chemical Industries PLC, Millbank, Great Britain

[21] Appl. No.: 988,648

[22] Filed: Dec. 10, 1992

[30] Foreign Application Priority Data

Dec. 11, 1991 [GB] United Kingdom ............... 9126339

[51] Int. Cl.$^5$ .............................................. C07F 3/02
[52] U.S. Cl. .................................................. 260/665 G
[58] Field of Search ....................... 260/665 G, 665 R

[56] References Cited

U.S. PATENT DOCUMENTS

| | | | |
|---|---|---|---|
| 3,264,360 | 8/1966 | Nudenberg et al. | 260/665 G |
| 3,597,488 | 8/1971 | Shepherd | 260/665 G |
| 3,706,809 | 12/1972 | Moroe et al. | 260/665 G X |
| 3,758,620 | 9/1973 | Vit | 260/665 G |
| 4,105,703 | 8/1978 | Motta | 260/665 G |
| 4,187,254 | 2/1980 | Bujadoux et al. | 260/665 G |
| 4,327,215 | 4/1982 | Hickmann et al. | 546/176 |
| 4,914,221 | 4/1990 | Winkler et al. | 556/436 |
| 4,942,244 | 7/1990 | Buschmann et al. | 548/268.2 |
| 5,158,702 | 10/1992 | Haas et al. | 252/299.6 |
| 5,169,958 | 12/1992 | Isak et al. | 549/499 |
| 5,175,167 | 12/1992 | Zipperer et al. | 514/277 |

FOREIGN PATENT DOCUMENTS 415247 8/1990 European Pat. Off. .
260277 9/1988 German Democratic Rep. .

OTHER PUBLICATIONS

Chemical & Engineering News, 69 (23), pp. 13-16 (Jun. 10, 1991).

Primary Examiner—Arthur C. Prescott
Attorney, Agent, or Firm—William E. Dickheiser

[57] ABSTRACT

Process for the preparation of compounds of formula (I):

$$Y-Mg-X \qquad (I)$$

wherein Y is allyl, or an optionally substituted phenyl or optionally substituted benzyl group, and X is a halogen, by reaction of a compound of formula (II):

$$Y-X \qquad (II)$$

wherein Y and X have the meanings given above, with magnesium in tertiary-butylmethyl ether solvent, characterized in that the molar ratio of magnesium to compound of formula (II) is from 1:1 to 2:1 and the reaction is carried out at 45° C. or above.

10 Claims, No Drawings

PREPARATION OF ORGANO-MAGNESIUM HALIDES

The present invention relates to a process for the preparation of allyl, aryl and aralkyl magnesium halides in ethereal solvent.

The preparation of allyl, aryl and aralkyl magnesium halides in ethereal solutions is well known. The use of diethyl ether solvent is common in Grignard reactions but has the significant hazard of a low flashpoint (−40° C.) and auto-ignition temperature (160° C.) making it essential to carry out the process in specially modified process equipment. Construction of a commercial plant to carry out the process with diethyl ether necessarily involves high capital cost. Thus, the use of diethyl ether is both hazardous to the process operators and expensive in terms of cost of process equipment. Other commonly used alternatives to diethyl ether such as tetrahydrofuran and glycoldimethyl ether result in high levels of dimerisation during the reaction, particularly in the preparation of benzylmagnesium halides. This can be avoided to some extent by using high ratios of magnesium to the allyl, aryl or aralkyl halide. However, this causes the process to be more expensive and provides the further problem of disposing of the magnesium after the reaction.

EP 415 247 describes the use of tertiary-butylmethyl ether (t-Bu-O-Me) as an alternative solvent to the commonly used solvents in the Grignard reaction. The disclosure demonstrates that at molar ratios of 2.5:1 to 20:1 (particularly 5:1 to 12:1) of magnesium to starting material the yield of Grignard product and amount of dimerisation is at the level expected when using diethyl ether as the solvent. The process is technically safer since this solvent has a flashpoint of −10° C. and auto-ignition temperature of 460° C., but it also has the significant disadvantage that a high molar ratio of magnesium to starting material is needed to suppress dimerisation.

It has now been found that tertiary-butylmethyl ether can be used in an improved process to give high yields of Grignard products and with a very low amount of dimerisation in reactions using magnesium and starting materials in equimolar or nearly equimolar amounts.

Accordingly the present invention provides for a process for the preparation of compounds of formula (I):

$$Y-Mg-X \quad \text{(I)}$$

wherein Y is allyl, or an optionally substituted phenyl or optionally substituted benzyl group, and X is a halogen, by reaction of a compound of formula (II):

$$Y-X \quad \text{(II)}$$

wherein Y and X have the meanings given above, with magnesium in tertiary-butylmethyl ether solvent, characterised in that the molar ratio of magnesium to compound of formula (II) is from 1:1 to 2:1 and the reaction is carried out at 45° C. or above.

The halogen X is suitably fluorine, chlorine or bromine.

Examples of suitable substituents for the phenyl and for the phenyl moiety of the benzyl are halogen; alkyl, preferably $C_{1-8}$ alkyl, for example, methyl, ethyl, propyl (iso- or n-) or butyl (iso-, sec-, t-, or n-) in the ortho or para positions on the ring; haloalkyl, preferably $C_{1-6}$ haloalkyl, with fluorine or chlorine as the halogen, for example, trifluoromethyl, or pentafluoroethyl; alkoxy, preferably $C_{1-6}$ alkoxy, for example, methoxy or ethoxy; haloalkoxy, preferably $C_{1-6}$ haloalkoxy with fluorine or chlorine as the halogen, for example, tetrafluoroethoxy; trifluoromethyl; nitro; phenyl and phenoxy, optionally substituted with halogen, for example, fluorine, chlorine or bromine.

The alkyl moiety of the benzyl can be substituted with alkyl, for example, methyl or ethyl.

When the phenyl group, or the phenyl moiety of the benzyl group is substituted with halogen, it is preferably substituted with fluorine, chlorine or bromine in one or more of the ortho, meta or para positions on the ring. Examples are 2-chlorophenyl, 3-chlorophenyl, 4-chlorophenyl, 2,4-dichlorophenyl, 2,6-dichlorophenyl, 2-fluorophenyl, 3-fluorophenyl, 4-fluorophenyl, 2,4-difluorophenyl, 2,6-difluorophenyl, 2-chloro-4-fluorophenyl, 2-chloro-6-fluorophenyl, 2-chlorobenzyl, 3-chlorobenzyl, 4-chlorobenzyl, 2,4-dichlorobenzyl, 2,6-dichlorobenzyl, 2-fluorobenzyl, 3-fluorobenzyl, 4-fluorobenzyl, 2,4-difluorobenzyl, 2,6-difluorobenzyl.

The reaction is preferably carried out at a temperature of from 45° C. to 100° C., more specifically from 45° C. to 60° C. and especially from 45° C. to the boiling point of tertiary-butylmethyl ether (55° C.). In practice, the reaction is preferably carried out under reflux conditions, which are from 50°–55° C.

The molar ration of magnesium to compound of formula (II) is preferably a slight excess of magnesium. Preferred molar ratios are from 1:1 to 2:1. Particular preferred are ratios from 1:1 to 1.5:1 and especially preferred are ratios from 1.01:1 to 1.25:1.

EP 415 247 discloses the use of tertiary-butylmethyl ether as an alternative solvent to the commonly used solvents in the Grignard reaction. The following table compares published data for tertiary-butylmethyl ether and diethyl ether with data from Examples 1 and 2 given herein. The reactions have been carried out using 2-chlorobenzyl chloride as the starting material of formula (II).

TABLE 1

| Solvent | ratio of Mg: (II) | % conversion of (II) | % dimerisation | % yield of (I) | reaction temp (°C.) |
|---|---|---|---|---|---|
| t-Bu-0-Me* | 1.20:1 | >95 | 10–15 | 75–80 | 35 |
| t-Bu-0-Me* | 6.00:1 | 95 | 0–5 | 85–90 | 35 |
| t-Bu-0-Me** | 1.03:1 | >99 | 0.4 | 93.4 | 50–55 |
| t-Bu-0-Me** | 1.24:1 | >99 | 2.0 | 83.4~ | 45–50 |
| t-Bu-0-Me** | 1.04:1 | >99 | 2.0 | 79.4~ | 45–50 |
| diethyl ether* | 1.20:1 | 98.7 | <5 | 85–90 | 35 |

Source
*EP 415 247
**Examples 1 and 2
~yield of epoxide using (I) (see Examples 1 and 2)

Table 1 demonstrates that using the solvent tertiary-butylmethyl ether under the conditions given in EP 415 247, the level of magnesium has to be maintained in significant excess compared to the starting material in order to approach the levels of yield of Grignard product and dimer by-product which are obtained when using diethyl ether. However, by raising the temperature of the reaction, it is surprisingly found that tertiary-butylmethyl ether is at least as effective as the solvent diethyl ether resulting in high yields of product with low amounts of dimerisation.

Therefore, under these process conditions the use of tertiary-butylmethyl ether as solvent maintains high yield and has the significant advantage lowering costs and hazards which are associated with using either diethyl ether or tertiary-butylmethyl ether under the preferred conditions disclosed in EP 415 247.

The following examples illustrate the invention. The examples demonstrate the preparation of the epoxide via the formation of the compound of formula (I). The epoxide is an important intermediate in the preparation of fungicidal compounds, as disclosed in EP-A-15756.

EXAMPLE 1

Preparation of 2-chlorobenzyl magnesium chloride

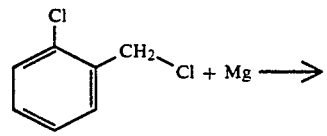

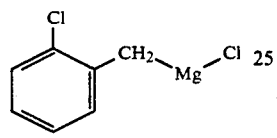

| REAGENTS | Wt (g) | MW | Moles | Mols Ratio |
| --- | --- | --- | --- | --- |
| 2-Chlorobenzyl chloride | 41.1 | 161 | 0.255 | 1.00 |
| Magnesium | 6.4 | 24.3 | 0.264 | 1.04 |
| Tertiary-butylmethyl ether | 190 | 88 | 2.159 | 8.47 |

METHOD

Under a nitrogen atmosphere, 60 g of tertiary-butyl methyl ether and 6.4 g of magnesium were stirred together and 6 g of preformed Grignard reagent solution was added, followed by 4 g of 2-chlorobenzyl chloride. A temperature rise of approximately 15° C. was noted. The rest of the tertiary-butylmethyl ether (130 g) was then added and the reaction heated to 50°-55° C. The rest of the 2-chlorobenzyl chloride (37.1 g) was added over a period of 1 hour during which the temperature was maintained at 50°-55° C. After a further 1 hour a GLC test showed consumption of 99.6% of the 2-chlorobenzyl chloride.

The reaction mixture was quenched by cautious addition of a mixture of concentrated hydrochloric acid (65 g) and water (1000 ml). The aqueous phase was separated off and extracted twice with tertiary-butylmethyl ether. The organic layers were combined and the solvent removed on a rotary evaporator to give 33.6 g of a yellow oil containing 87% of 2-chlorotoluene and 3% of 2-chlorobenzyl alcohol, equivalent to 93.4% yield of 2-chlorobenzyl magnesium chloride from 2-chlorobenzyl chloride.

Yield of Grignard reagent = 93.4%
% of dimer present after reaction = 0.4%.

EXAMPLE 2

Preparation of 1,2-epoxy-2-(2-chlorobenzyl)-3,3-dimethyl butane

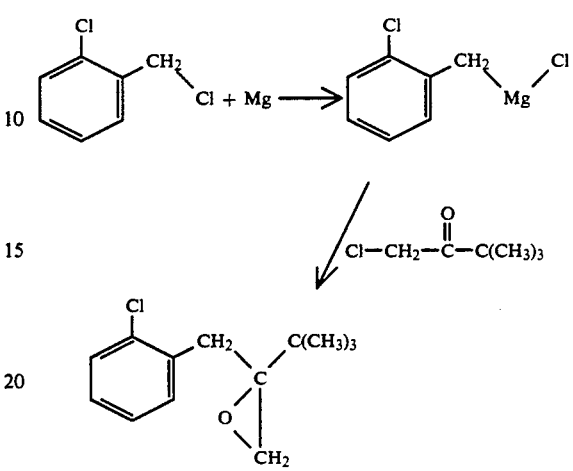

| REAGENTS | Wt (g) | MW | Moles | Mols Ratio |
| --- | --- | --- | --- | --- |
| 2-Chlorobenzyl chloride | 41.1 | 161 | 0.255 | 1.05 |
| Magnesium | 7.4 | 24.3 | 0.317 | 1.30 |
| Tertiary-butylmethyl ether | 190 | 88 | 2.159 | 8.89 |
| Monochloropinacolone | 32.6 | 134.5 | 0.243 | 1 |

METHOD

Under a nitrogen atmosphere, 60 g of tertiary-butylmethyl ether and 7.4 g of magnesium were stirred together in 5 g of preformed Grignard reagent solution. 2-Chlorobenzyl chloride (2.0 g) was added to the reaction mixture and a temperature rise of approximately 5° C. was noted. The rest of the tertiary-butylmethyl ether (130 g) was then added and the reaction mixture heated to 45°-50° C. The rest of the 2-chlorobenzyl chloride (39.1 g) was added over a period of 1 hour during which the temperature was maintained at 45°-50° C. After a further 30 minutes, a GLC test showed virtual consumption of all the 2-chlorobenzyl chloride.

Monochloropinacolone was added over 1 hour at 30°-35° C. After 1 hour the mixture was quenched with a solution of ammonium chloride (25 g) in water (200 g) and the tertiary-butylmethyl ether was distilled off. The resulting mixture was allowed to settle at 70° C. and the lower aqueous layer separated off to leave 60 g of product as a yellow oil.

Yield of epoxide = 83.4%
% of dimer present after reaction = 2.0%.

EXAMPLE 3

Preparation of 1,2-epoxy-2-(2-chlorobenzyl)-3,3-dimethyl butane

| REAGENTS | Wt (g) | MW | Moles | Mols Ratio |
| --- | --- | --- | --- | --- |
| 2-Chlorobenzyl chloride | 41.1 | 161 | 0.255 | 1.05 |
| Magnesium | 6.4 | 24.3 | 0.264 | 1.09 |
| Tertiary-butylmethyl ether | 190 | 88 | 2.159 | 8.89 |
| Monochloropinacolone | 32.6 | 134.5 | 0.243 | 1 |

METHOD

Under a nitrogen atmosphere, 60 g of tertiary-butylmethyl ether and 6.4 g of magnesium were stirred together in 5 g of preformed Grignard reagent solution. 2-Chlorobenzyl-chloride (4.0 g) was added to the reaction mixture and a temperature rise of approximately 20° C. was noted. The rest of the tertiary-butylmethyl ether (130 g) was then added and the reaction mixture heated to 45°-50° C. The rest of the 2-chlorobenzyl chloride (37.1 g) was added over a period of 1 hour during which the temperature was maintained at 45°-50° C. After a further 30 minutes, a GLC test showed virtual consumption of all the 2-chlorobenzyl chloride.

Monochloropinacolone was added over 1 hour at 30°-35° C. After 1 hour the mixture was quenched with a solution of ammonium chloride (25 g) in water (200 g) and the tertiary-butylmethyl ether was distilled off. The resulting mixture was allowed to settle at 70° C. and the lower aqueous layer separated off to leave 53.1 g of product as a yellow oil.

Yield of epoxide = 79.4%

% of dimer present after reaction = 2.0%.

We claim:

1. Process for the preparation of compounds of formula (I):

Y—Mg—X    (I)

wherein Y is allyl, or an optionally substituted phenyl or optionally substituted benzyl group, and X is a halogen, by reaction of a compound of formula (II):

Y—X    (II)

wherein Y and X have the meanings given above, with magnesium in tertiary-butylmethyl ether solvent, characterised in that the molar ratio of magnesium to compound of formula (II) is from 1:1 to 2:1 and the reaction is carried out at 45° C. or above.

2. Process according to claim 1 wherein the reaction is carried out at 45°-100° C.

3. Process according to claim 1 wherein the reaction is carried out at 45°-60° C.

4. Process according to claim 1 wherein the reaction is carried out at temperatures from 45° C. to the boiling point of tertiary-butylmethyl ether.

5. Process according to claim 1 wherein the reaction is carried out at 50°-55° C.

6. Process according to claim 1 wherein the molar ration of magnesium to compound of formula (II) is from 1:1 to 1.5:1.

7. Process according to claim 1 wherein the molar ratio of magnesium to compound of formula (II) is from 1.01:1 to 1.25:1.

8. Process according claim 1 wherein Y is phenyl or benzyl optionally substituted with halogen; $C_{1-8}$ alkyl; $C_{1-6}$ haloalkyl; $C_{1-6}$ alkoxy; $C_{1-6}$ haloalkoxy; nitro; phenyl or phenoxy, optionally substituted with halogen.

9. Process according to claim 8 wherein Y is 2-chlorobenzyl.

10. Process according to claim 1 wherein X is chlorine.

* * * * *